(12) United States Patent
Taniguchi et al.

(10) Patent No.: US 10,370,313 B2
(45) Date of Patent: Aug. 6, 2019

(54) MANUFACTURING METHOD OF PURIFIED 1-CHLORO-2,3,3,3-TETRAFLUOROPROPENE AND PURIFIED 1-CHLORO-2,3,3,3-TETRAFLUOROPROPENE (Z)

(71) Applicant: AGC Inc., Chiyoda-ku (JP)

(72) Inventors: Tomoaki Taniguchi, Chiyoda-ku (JP); Jumpei Nomura, Chiyoda-ku (JP); Takayuki Sakai, Chiyoda-ku (JP); Takashi Hayase, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/105,407

(22) Filed: Aug. 20, 2018

(65) Prior Publication Data

US 2019/0002375 A1    Jan. 3, 2019

Related U.S. Application Data

(63) Continuation of application No. PCT/JP2017/007018, filed on Feb. 24, 2017.

(30) Foreign Application Priority Data

Feb. 26, 2016  (JP) .................................. 2016-035365

(51) Int. Cl.
| | | |
|---|---|---|
| C07C 17/386 | (2006.01) | |
| C07C 17/383 | (2006.01) | |
| C07C 17/38 | (2006.01) | |
| C07C 21/18 | (2006.01) | |
| B01D 3/14 | (2006.01) | |
| B01D 11/04 | (2006.01) | |

(52) U.S. Cl.
CPC ............ *C07C 17/383* (2013.01); *C07C 17/38* (2013.01); *C07C 17/386* (2013.01); *C07C 21/18* (2013.01); *B01D 3/143* (2013.01); *B01D 11/04* (2013.01); *B01D 2257/206* (2013.01); *Y02P 20/124* (2015.11)

(58) Field of Classification Search
CPC ...... C07C 17/38; C07C 17/383; C07C 17/386
See application file for complete search history.

(56) References Cited

U.S. PATENT DOCUMENTS

| 6,179,967 B1 | 1/2001 | Nishimura et al. |
|---|---|---|
| 2010/0076231 A1 | 3/2010 | Nappa et al. |
| 2011/0009678 A1* | 1/2011 | Bonnet .................. C07C 17/358 570/136 |
| 2011/0270001 A1* | 11/2011 | Ishihara ................. C07C 17/386 570/178 |
| 2011/0319678 A1 | 12/2011 | Seki et al. |
| 2012/0215037 A1 | 8/2012 | Sun et al. |
| 2013/0105296 A1 | 5/2013 | Chaki et al. |
| 2013/0317262 A1 | 11/2013 | Kurashima et al. |
| 2015/0259267 A1 | 9/2015 | Sun et al. |

FOREIGN PATENT DOCUMENTS

| CN | 105753634 A | 7/2016 |
|---|---|---|
| EP | 0 626 362 A1 | 11/1994 |
| EP | 2 586 762 A1 | 5/2013 |
| EP | 2 671 860 A1 | 12/2013 |
| JP | 46-14725 | 4/1971 |
| JP | 3-52828 | 3/1991 |
| JP | 7-133240 | 5/1995 |
| JP | 8-169850 | 7/1996 |
| JP | 8-193039 | 7/1996 |
| JP | 9-20765 | 1/1997 |
| JP | 11-43451 | 2/1999 |
| JP | 2010-202640 | 9/2010 |
| JP | 2010-531925 | 9/2010 |
| JP | 2013-521275 | 6/2013 |
| JP | 2014-513673 | 6/2014 |
| JP | 5713016 | 5/2015 |
| JP | 2016-130236 | 7/2016 |
| JP | 5971123 | 8/2016 |
| JP | 2017-7946 | 1/2017 |
| WO | WO 91/01287 | 2/1991 |
| WO | WO 2008/054778 A2 | 5/2008 |
| WO | WO 2009/035893 A1 | 3/2009 |
| WO | WO 2010/090086 A1 | 8/2010 |
| WO | WO 2011/162336 A1 | 12/2011 |
| WO | WO 2012/011609 A1 | 1/2012 |
| WO | WO 2012/105700 A1 | 8/2012 |
| WO | WO 2012/115930 A1 | 8/2012 |
| WO | WO 2015/072460 A1 | 5/2015 |

OTHER PUBLICATIONS

International Search Report dated May 9, 2017 in PCT/JP2017/007018, filed on Feb. 24, 2017 (with English Translation).
Written Opinion dated May 9, 2017 in PCT/JP2017/007018, filed on Feb. 24, 2017.

* cited by examiner

*Primary Examiner* — Medhanit W Bahta
(74) *Attorney, Agent, or Firm* — Oblon, McClelland, Maier & Neustadt, L.L.P.

(57) ABSTRACT

There is provided a method of efficiently manufacturing purified 1224yd containing 1224yd at a high concentration from a mixture containing 1224yd and a compound that forms an azeotropic composition or an azeotropic-like composition with 1224yd. A manufacturing method of purified 1224yd, includes making a first mixture of 1224yd and a compound (X1) forming an azeotropic composition or an azeotropic-like composition with 1224yd to be brought into contact with a first extraction solvent to obtain purified 1224yd not substantially containing the compound (X1).

20 Claims, No Drawings

US 10,370,313 B2

MANUFACTURING METHOD OF PURIFIED 1-CHLORO-2,3,3,3-TETRAFLUOROPROPENE AND PURIFIED 1-CHLORO-2,3,3,3-TETRAFLUOROPROPENE (Z)

CROSS-REFERENCE TO RELATED APPLICATIONS

This application is a continuation of prior International Application No. PCT/JP2017/007018, filed on Feb. 24, 2017 which is based upon and claims the benefit of priority from Japanese Patent Application No. 2016-035365, filed on Feb. 26, 2016; the entire contents of all of which are incorporated herein by reference.

TECHNICAL FIELD

The present invention relates to a method of manufacturing purified 1-chloro-2,3,3,3-tetrafluoropropene and purified 1-chloro-2,3,3,3-tetrafluoropropene (Z).

BACKGROUND

Recently, as a working fluid for a heat cycle system such as a refrigerant for a refrigerator, a refrigerant for an air-conditioning apparatus, a working fluid for a power generation system (such as an exhaust heat recovery power generation), a working fluid for a latent heat transport apparatus (such as a heat pipe), or a secondary cooling medium, expectations are concentrated on hydrofluoroolefin (HFO), namely, hydrofluorocarbon (HFC) having a carbon-carbon double bond. HFO attracts attention as a working fluid having less effect on the ozone layer and less effect on global warming since the carbon-carbon double bond is likely to be decomposed by OH radicals in the air.

As a working fluid having not only less effect on the ozone layer and global warming but also low combustibility, there are hydrochlorofluoroolefin (HCFO) such as hydrochlorofluoropropene and chlorofluoroolefin (CFO) having a high ratio of halogen which reduces combustibility and having a carbon-carbon double bond which is likely to be decomposed by OH radicals in the air. Further, as one kind of hydrochlorofluoropropene, there is known 1-chloro-2,3,3,3-tetrafluoropropene (HCFO-1224yd).

In the present specification, regarding halogenated hydrocarbon, an abbreviated name of the compound is mentioned in parentheses behind a compound name, and the abbreviated name is used instead of the compound name according to need. Further, only numeric characters and small characters of alphabet behind a hyphen (-) ("1224yd" in "HCFO-1224yd", for example) are sometimes used as the abbreviated name.

Note that in 1224yd, a Z-isomer and an E-isomer which are geometric isomers exist according to positions of substituents bonded to carbon having a double bond. When the compound name or the abbreviated name of the compound is used unless otherwise stated regarding the compound such as 1224yd with respect to which the Z-isomer and the E-isomer exist in the present specification, the Z-isomer, the E-isomer, or a mixture having an arbitrary ratio of the Z-isomer and the E-isomer is indicated. When (Z) or (E) is denoted behind the compound name or the abbreviated name of the compound, a Z-isomer or an E-isomer of each compound is indicated.

It is known that 1224yd can be obtained as an intermediate in a process of manufacturing 2,3,3,3-tetrafluoropropene (1234yf) which has been greatly expected as a new refrigerant in recent years from 1,1-dichloro-2,3,3,3-tetrafluoropropene (1214ya).

Specifically, there has been conventionally known a method of manufacturing 1214ya in a manner that 1,1-dichloro-2,2,3,3,3-pentafluoropropane (225ca) or the like is used as a raw material, and is subjected to a dehydrofluorination reaction in an alkaline aqueous solution in the presence of a phase-transfer catalyst or through a gas phase reaction in the presence of a catalyst such as chromium, iron, copper, or activated carbon, and the obtained 1214ya is reduced by using hydrogen in the presence of a catalyst, to be converted into 1234yf. Besides, as an intermediate in this reduction reaction, 1224yd can be obtained. Further, in this reduction reaction, a lot of kinds of fluorine-containing compounds are generated as by-products, other than 1224yd.

Here, 1224yd being the intermediate can be separated from 1214ya being an unreacted raw material and 1234yf being an object, through normal distillation, but, a fraction obtained by this distillation operation contains, other than 1224yd, 1-chloro-1,2,2,3,3,3-hexafluoropropane (226ca), 1-chloro-1,1,2,2,3,3-hexafluoropropane (226cb), 1-chloro-1,3,3,3-tetrafluoropropene (1224zb), and 2-chloro-1,3,3,3-tetrafluoropropene (1224xe) being by-products of the reduction reaction described above.

As a method of separating the by-products from the composition containing such by-products (referred to as "1224yd composition", hereinafter), distillation can be considered, and a compound such as the aforementioned 226ca has a boiling point close to a boiling point of 1224yd (a boiling point of 1224yd (Z) is 15° C., and a boiling point of 1224yd (E) is 19° C.). Further, the above-described compound forms an azeotropic composition or an azeotropic-like composition with 1224yd, so that it is not easy to separate the above-described compound from the 1224yd composition. Specifically, when a composition containing 1224yd at a high concentration is tried to be obtained from the 1224yd composition through a normal distillation method, a distillation apparatus with a very large number of stages is required, so that generally, it has been difficult to perform the separation through the distillation.

As a method of separating a composition which is difficult to be separated through normal distillation, there has been conventionally known an extractive distillation method in which a solvent having an affinity to a partial component contained in a composition is brought into contact with the composition to perform distillation (refer to Patent Reference 1 (JP-A No. H09-020765), for example). However, it has been unknown and also it has been difficult to predict that what kind of solvent is used to obtain the composition containing 1224yd at a high concentration by separating the by-products from the 1224yd composition efficiently, for example, in a distillation column with a small number of stages.

Further, 1224yd (Z) has chemical stability higher than that of 1224yd (E), and thus is a compound which is more preferable to be used as a working fluid for a heat cycle, however, an operation in which the composition containing 1224yd (Z) at a high concentration is obtained by separating only 1224yd (Z) from the 1224yd composition has not been conducted.

SUMMARY OF THE INVENTION

The present invention has been made to solve the above-described problems, and an object thereof is to provide a method of efficiently manufacturing a composition containing 1-chloro-2,3,3,3-tetrafluoropropene (HCFO-1224yd, which is also referred to as 1224yd) at a high concentration (referred to as "purified 1224yd", hereinafter) from a mixture containing 1224yd and a compound that forms an azeotropic composition or an azeotropic-like composition with 1224yd.

The present invention also has an object to provide a method of efficiently manufacturing a composition containing 1224yd (Z) at a high concentration (referred to as "purified 1224yd (Z)", hereinafter) from a mixture containing 1224yd (Z) and a compound that forms an azeotropic composition or an azeotropic-like composition with 1224yd (Z).

In the present specification, regarding halogenated hydrocarbon, an abbreviated name of the compound is mentioned in parentheses behind a compound name, and the abbreviated name is used instead of the compound name according to need. Further, only numeric characters and small characters of alphabet behind a hyphen (-) ("1224yd" in "HCFO-1224yd", for example) are sometimes used as the abbreviated name.

Note that in 1224yd, a Z-isomer and an E-isomer which are geometric isomers exist according to positions of substituents bonded to carbon having a double bond. When the compound name or the abbreviated name of the compound is used unless otherwise stated regarding the compound such as 1224yd with respect to which the Z-isomer and the E-isomer exist in the present specification, the Z-isomer, the E-isomer, or a mixture having an arbitrary ratio of the Z-isomer and the E-isomer is indicated. When (Z) or (E) is denoted behind the compound name or the abbreviated name of the compound, a Z-isomer or an E-isomer of each compound is indicated.

The present invention provides a method of manufacturing purified 1224yd and purified 1224yd (Z) having configurations of the following [1] to [12].

[1] A manufacturing method of purified 1224yd, including making a first mixture of 1224yd and a compound (X1) forming an azeotropic composition or an azeotropic-like composition with 1224yd to be brought into contact with a first extraction solvent to obtain purified 1224yd not substantially containing the compound (X1).

[2] A manufacturing method of purified 1224yd (Z), including making a second mixture of 1224yd (Z) and a compound (X2) forming an azeotropic composition or an azeotropic-like composition with 1224yd (Z) to be brought into contact with a second extraction solvent to obtain purified 1224yd (Z) not substantially containing the compound (X2).

[3] The manufacturing method according to [1], wherein the compound (X1) is a compound which exhibits a relative volatility between 1224yd and the compound (X1) in the first mixture of 0.9 to 1.1.

[4] The manufacturing method according to [2], wherein the compound (X2) is a compound which exhibits a relative volatility between 1224yd (Z) and the compound (X2) in the second mixture of 0.9 to 1.1.

[5] The manufacturing method according to [1], wherein the first extraction solvent is a solvent capable of making the relative volatility between 1224yd and the compound (X1) to be smaller than 0.85 or larger than 1.15.

[6] The manufacturing method according to [2], wherein the second extraction solvent is a solvent capable of making the relative volatility between 1224yd (Z) and the compound (X2) to be smaller than 0.85 or larger than 1.15.

[7] The manufacturing method according to [1], wherein the first extraction solvent is one selected from the group consisting of an alcohol having 1 to 3 carbon atoms and a carbonyl compound having 2 to 4 carbon atoms in total excluding a carbon atom of a carbonyl group.

[8] The manufacturing method according to [2], wherein the second extraction solvent is one selected from the group consisting of an alcohol having 1 to 3 carbon atoms and a carbonyl compound having 2 to 4 carbon atoms in total excluding a carbon atom of a carbonyl group.

[9] The manufacturing method according to [1], wherein the method includes obtaining a third mixture by mixing the first mixture and the first extraction solvent, to make the first mixture and the first extraction solvent to be brought into contact with each other, and distilling the third mixture.

[10] The manufacturing method according to [9], wherein the mixing is performed so that a molar ratio of the first extraction solvent with respect to 1224yd in the first mixture becomes 0.4 to 200.

[11] The manufacturing method according to [2], wherein the method includes obtaining a fourth mixture by mixing the second mixture and the second extraction solvent, to make the second mixture and the second extraction solvent to be brought into contact with each other, and distilling the fourth mixture.

[12] The manufacturing method according to [11], wherein the mixing is performed so that a molar ratio of the second extraction solvent with respect to 1224yd (Z) in the second mixture becomes 0.4 to 200.

In the present specification, "purified 1224yd" indicates a 1224yd composition containing 1224yd at a high concentration or pure 1224yd. The same applies to purified 1224yd (Z).

In the present specification, "purified 1224yd not substantially containing a compound (X1)" indicates a 1224yd composition whose molar concentration of 1224yd is 99% or more or pure 1224yd. Further, "purified 1224yd (Z) not substantially containing a compound (X2)" indicates a 1224yd (Z) composition whose molar concentration of 1224yd (Z) is 97% or more (preferably 99% or more) or pure 1224yd (Z).

A relative volatility between 1224yd and the compound (X1) (referred to as "relative volatility r1", hereinafter) is represented by the following formula (1).

Relative volatility $r1$=(molar fraction (mol %) of 1224$yd$ in gas phase part/molar fraction (mol %) of 1224$yd$ in liquid phase part)/(molar fraction (mol %) of compound ($X1$) in gas phase part/molar fraction (mol %) of compound ($X1$) in liquid phase part) (1)

When 1224yd is a mixture of 1224yd (Z) and 1224yd (E), a molar fraction of 1224yd is the sum of a molar fraction of 1224yd (Z) and a molar fraction of 1224yd (E).

A relative volatility between 1224yd (Z) and the compound (X2) (referred to as "relative volatility r2", hereinafter) is represented by the following formula (2).

Relative volatility $r2$=(molar fraction (mol %) of 1224$yd$ (Z) in gas phase part/molar fraction (mol %) of 1224$yd$ (Z) in liquid phase part)/ (molar fraction (mol %) of compound ($X2$) in gas phase part/molar fraction (mol %) of compound ($X2$) in liquid phase part) (2)

According to the present invention, it is possible to efficiently separate a compound (X1) from a composition containing 1224yd and the compound (X1) forming an azeotropic composition or an azeotropic-like composition with 1224yd, to thereby manufacture purified 1224yd not substantially containing the compound (X1) and contains 1224yd at a quite high concentration.

Further, according to the present invention, it is possible to efficiently separate a compound (X2) from a composition containing 1224yd (Z) and the compound (X2) forming an azeotropic composition or an azeotropic-like composition with 1224yd (Z), to thereby obtain purified 1224yd (Z) not substantially containing the compound (X2) and contains 1224yd (Z) at a quite high concentration.

MODES FOR CARRYING OUT THE INVENTION

A manufacturing method of purified 1224yd being a first embodiment of the present invention is a method in which a first mixture of 1224yd and a compound (X1) forming an azeotropic composition or an azeotropic-like composition with 1224yd is brought into contact with a first extraction solvent to manufacture purified 1224yd not substantially containing the compound (X1).

A manufacturing method of purified 1224yd (Z) being a second embodiment of the present invention is a method in which a second mixture of 1224yd (Z) and a compound (X2) forming an azeotropic composition or an azeotropic-like composition with 1224yd (Z) is brought into contact with a second extraction solvent to manufacture purified 1224yd (Z) not substantially containing the above-described compound (X2).

In the manufacturing method of the first embodiment of the present invention, the contact between the first mixture made of 1224yd and the compound (X1) and the first extraction solvent may be carried out in the presence of a compound other than the first mixture and the first extraction solvent, as long as the contact is performed. Specifically, it is possible to carry out the first embodiment of the present invention by using a 1224yd composition containing the first mixture and optionally containing a compound other than the first mixture as a raw material.

In like manner, in the manufacturing method of the second embodiment of the present invention, the contact between the second mixture made of 1224yd (Z) and the compound (X2) and the second extraction solvent may be carried out in the presence of a compound other than the second mixture and the second extraction solvent, as long as the contact is performed. Specifically, it is possible to carry out the second embodiment of the present invention by using a 1224yd (Z) composition containing the second mixture and optionally containing a compound other than the second mixture as a raw material.

1224yd and the compound (X1) are both compounds obtained as intermediates when reducing 1214ya by hydrogen to manufacture 1234yf, for example, and the compound (X1) can form an azeotropic composition or an azeotropic-like composition with 1224yd. Therefore, the 1224yd composition made of the first mixture of 1224yd and the compound (X1) or containing the first mixture and a compound other than the first mixture can be obtained in a process of manufacturing 1234yf from 1214ya in the following manner. The 1224yd (Z) composition made of the second mixture of 1224yd (Z) and the compound (X2) or containing the second mixture and a compound other than the second mixture can also be obtained in a process of manufacturing 1234yf from 1214ya, in a similar manner.

Here, 1214ya being a starting material can be obtained in a manner that, for example, an isomer mixture mainly containing 225ca is subjected to a dehydrofluorination reaction in an alkaline aqueous solution in the presence of a phase-transfer catalyst or through a gas phase reaction in the presence of a catalyst such as chromium, iron, copper, or activated carbon.

In order to manufacture 1234yf from 1214ya, hydrogen is made to react with 1214ya in the presence of a catalyst, as represented by the following reaction formula.

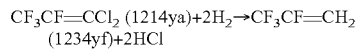

$$CF_3CF=CCl_2 \ (1214ya) + 2H_2 \rightarrow CF_3CF=CH_2 \ (1234yf) + 2HCl$$

As the catalyst, there can be cited a catalyst in which palladium is carried on a carrier or a catalyst in which a metal mixture containing palladium as a main component and at least one selected from the group consisting of a group 10 element other than palladium, a group 8 element, a group 9 element, and gold added to palladium, is carried on a carrier. As the carrier on which the above-described palladium or metal mixture containing palladium as a main component is carried, it is possible to use activated carbon, a metal oxide such as alumina, zirconia, or silica, or the like.

The generation reaction of 1234yf represented by the aforementioned reaction formula is carried out in a manner that, at 130° C. or less, 1214ya and hydrogen which are heated to be turned into a gaseous state are passed inside a reactor in which the catalyst is filled, and brought into contact with the catalyst (gas phase reduction method). The aforementioned generation reaction is preferably carried out at not less than 50° C. nor more than 125° C. Normally, the reaction sufficiently progresses when a reaction pressure is an atmospheric pressure or own-pressure. A contact time of the gaseous 1214ya and hydrogen with respect to the catalyst may be normally set in a range of 4 to 60 seconds and preferably set in a range of 8 to 40 seconds. The above-described reaction may be carried out by diluting a reaction system using an inert gas such as nitrogen, in order to regulate the excessive increase in the temperature.

A distillation residue remained after performing distillation and removal of 1234yf from a reaction mixture obtained by making 1214ya to be subjected to the reduction reaction as described above, contains 1214ya being an unreacted raw material, 1224yd being an intermediate product, 226ca, 226cb, 1224zb, 1224xe being by-products, and so on. By separating 1214ya being the unreacted raw material from the aforementioned distillation residue through normal distillation, it is possible to obtain the 1224yd composition to be a raw material in the manufacturing method of the first embodiment of the present invention.

Further, the 1224yd composition to be the raw material in the manufacturing method of the first embodiment of the present invention can also be manufactured in a manner that 1,2-dichloro-2,3,3,3-tetrafluoropropane (234bb) is brought into contact with a base dissolved in a solvent in a liquid phase to perform a dehydrochlorination reaction of 234bb, as will be described below. A method of obtaining 234bb is not particularly limited, and it may be a method in which 1234yf is reacted with chlorine, for example.

As the above-described base, at least one selected from the group consisting of a metal hydroxide, a metal oxide, and a metal carbonate is preferable, at least one selected from alkali metal hydroxides is more preferable, and either or both of potassium hydroxide and sodium hydroxide is/are still more preferable.

The solvent to dissolve the base is not particularly limited as long as it is a solvent capable of dissolving a predetermined amount of the above-described base and does not contribute to the above-described reaction. As the solvent, water is preferable because the solubility thereof with respect to the above-described base is high and water is inert with respect to the above-described reaction. As the base dissolved in the solvent described above, an aqueous solution of the alkali metal hydroxide is preferable, and an aqueous solution of potassium hydroxide or an aqueous solution of sodium hydroxide is more preferable. A ratio of the base with respect to 234bb is preferably 0.2 mol to 2.5 mol, and more preferably 0.5 mol to 2.0 mol with respect to 1 mol of 234bb, from a viewpoint of the conversion ratio of 234bb and the selectivity of 1224yd.

1224yd obtained by this method is likely to contain 1224yd (Z) at a concentration higher than that of 1224yd (E).

Further, the 1224yd (Z) composition to be a raw material in the manufacturing method of the second embodiment of the present invention can be obtained similarly to the 1224yd composition to be the raw material in the manufacturing method of the first embodiment of the present invention.

The compound (X1) that forms the azeotropic composition with 1224yd is a compound which exhibits the relative volatility r1 represented by the aforementioned formula (1) of 1.00 in the first mixture being the mixture of 1224yd and the compound (X1).

Further, the compound (X2) that forms the azeotropic composition with 1224yd (Z) is a compound which exhibits the relative volatility r2 represented by the aforementioned formula (2) of 1.00 in the second mixture being the mixture of 1224yd (Z) and the compound (X2).

The azeotropic composition has an advantage that when the composition is repeatedly evaporated and condensed, there is no composition change and thus excellent composition stability is provided, and when it is used for the application of refrigerant or the like, it can obtain performances in a quite stable manner. On the other hand, it is difficult to separate a plurality of components contained in the azeotropic composition through a normal distillation operation.

The compound (X1) that forms the azeotropic-like composition with 1224yd indicates a compound capable of forming a mixture having composition stability similar to that of the azeotropic composition with 1224yd. When the compound (X1) is a compound which exhibits the relative volatility r1 represented by the aforementioned formula (1) of 0.9 to 1.1 in the first mixture being the mixture of 1224yd and the compound (X1), the manufacturing method of the present invention is preferably adopted. It is more preferable that the compound (X1) is a compound which exhibits the relative volatility r1 of 0.95 to 1.05.

The compound that forms the azeotropic-like composition with 1224yd includes the compound (X1) that forms the azeotropic composition with 1224yd. The compound (X1) may be one kind or more.

The compound (X2) that forms the azeotropic-like composition with 1224yd (Z) indicates a compound capable of forming a mixture having composition stability similar to that of the azeotropic composition with 1224yd (Z). When the compound (X2) is a compound which exhibits the relative volatility r2 represented by the aforementioned formula (2) of 0.9 to 1.1 in the second mixture being the mixture of 1224yd (Z) and the compound (X2), the manufacturing method of the present invention is preferably adopted. It is more preferable that the compound (X2) is a compound which exhibits the relative volatility r2 of 0.95 to 1.05.

The compound that forms the azeotropic-like composition with 1224yd (Z) includes the compound (X2) that forms the azeotropic composition with 1224yd (Z). The compound (X2) may be one kind or more.

As the compound (X1) that forms the azeotropic composition or the azeotropic-like composition with 1224yd, there can be cited, for example, 226ca (boiling point of 20° C.), 226cb (boiling point of 21° C.), 1224zb (boiling point of 17° C.), and 1224xe (boiling point of 32.8° C.) being compounds which are formed as by-products in the process of manufacturing 1234yf. Further, as the compound (X2) that forms the azeotropic composition or the azeotropic-like composition with 1224yd (Z), there can be cited the aforementioned compound (X1), and 1224yd (E).

First Embodiment

A manufacturing method of purified 1224yd being a first embodiment of the present invention is a method in which a first mixture of 1224yd and a compound (X1) that forms an azeotropic composition or an azeotropic-like composition with 1224yd is brought into contact with a first extraction solvent to obtain purified 1224yd not substantially containing the above-described compound (X1).

The first extraction solvent is preferably one capable of making the relative volatility r1 greatly deviate from 1. When the relative volatility r1 greatly deviates from 1, the compound (X1) and 1224yd are easily separated, so that it is possible to efficiently manufacture purified 1224yd.

In the first embodiment, a relative volatility between 1224yd and the compound (X1) in a state where the first extraction solvent is not added is set to a relative volatility r11, the above-described relative volatility when the first extraction solvent is added is set to a relative volatility r12, and the relative volatility r11 and the relative volatility r12 are compared.

When the relative volatility r12 is larger than the relative volatility r11, this means that an affinity of the compound (X1) with respect to the first extraction solvent is higher than an affinity of 1224yd with respect to the first extraction solvent. By using the first extraction solvent capable of making the relative volatility r12 to be larger than the relative volatility r11, it is easy to obtain purified 1224yd in a gas phase part by efficiently separating 1224yd and the compound (X1) from the first mixture.

When the relative volatility r12 is smaller than the relative volatility r11, this means that the affinity of the compound (X1) with respect to the first extraction solvent is lower than the affinity of 1224yd with respect to the first extraction solvent. By using the first extraction solvent capable of making the relative volatility r12 to be smaller than the relative volatility r11, it is easy to obtain purified 1224yd in a liquid phase part.

From the above-described viewpoint, the first extraction solvent is preferably a solvent capable of making the relative volatility r1 to be smaller than 0.85 or larger than 1.15. The first extraction solvent is more preferably a solvent capable of making the relative volatility r1 to be equal to or smaller than 0.8 or equal to or larger than 1.20. When the relative volatility r1 is within the above-described range, it is easy to obtain purified 1224yd in the gas phase part or the liquid phase part.

From a viewpoint of efficiently performing distillation and separation in a recovery process of the solvent, the first extraction solvent preferably has a boiling point which is greatly different from boiling points of 1224yd and the compound (X1). From a viewpoint of productivity in the distillation and separation process, the boiling point of the first extraction solvent is preferably not too high.

The boiling point of the first extraction solvent is preferably in a range of 10 to 250° C. When the boiling point difference between the first extraction solvent, and 1224yd and the compound (X1) is taken into consideration, the boiling point of the first extraction solvent is more preferably 40 to 240° C. Note that a boiling point of a substance in the present specification is set to indicate a boiling point in an atmospheric pressure ($1.013 \times 10^5$ Pa) unless otherwise stated.

As the first extraction solvent, it is possible to use a saturated hydrocarbon having 5 to 12 carbon atoms, a halogenated hydrocarbon having 1 to 10 carbon atoms which does not have an ether bond, an alcohol having 1 to 3 carbon atoms, a carbonyl compound, and so on. As the saturated hydrocarbon having 5 to 12 carbon atoms, a linear saturated hydrocarbon compound having 6 to 10 carbon atoms is preferable. Concretely, hexane (68° C.) can be cited.

The halogenated hydrocarbon having 1 to 10 carbon atoms which does not have an ether bond is a compound in which 20 to 100% of hydrogen atoms in linear or branched saturated hydrocarbon substitute for halogen atoms, and a compound having no ether bond in a main chain or a side chain. A number of carbon atoms is preferably 2 to 8. Concretely, there can be cited chloroform (trichloromethane) (boiling point of 61.2° C.), 1,3-dichloro-1,1,2,2,3-pentafluoropropane (225cb) (boiling point of 202.9° C.), and 1214ya (boiling point of 46.4° C.). As the alcohol having 1 to 3 carbon atoms, alcohol having an aliphatic hydrocarbon group having 1 to 3 carbon atoms is preferable, a compound having a linear or branched aliphatic hydrocarbon group having 1 to 3 carbon atoms and having at least one hydroxyl group is preferable, and alcohol having a linear aliphatic hydrocarbon group having 1 to 3 carbon atoms is more preferable. Concretely, there can be cited methanol (boiling point of 64.7° C.), and ethanol (boiling point of 78.37° C.).

As the carbonyl compound, a carbonyl compound having 2 to 4 carbon atoms in total excluding a carbon atom of a carbonyl group is preferable. As the carbonyl compound, a compound represented by the following formula (11) is also preferable.

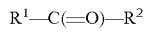

$R^1$—C(=O)—$R^2$   Formula (11)

In the formula (11), $R^1$ and $R^2$ indicate the same or different unsubstituted aliphatic hydrocarbon groups.

The carbonyl compound is preferably a carbonyl compound in which, in the formula (11), each of $R^1$ and $R^2$ is an unsubstituted aliphatic hydrocarbon group having 1 to 2 carbon atoms, and a total number of carbon atoms of $R^1$ and $R^2$ is 2 to 4. Concretely, there can be cited acetone (boiling point of 56° C.), diethylketone (boiling point of 101° C.), and methyl ethyl ketone (boiling point of 79.5° C.). As the first extraction solvent, it is preferable to use one kind selected from the alcohol having 1 to 3 carbon atoms, and the carbonyl compound.

As the first extraction solvent, it is preferable to use methanol, ethanol, or acetone, and it is more preferable to use methanol. One kind of the first extraction solvent may be used or two kinds or more thereof may be used in combination.

In the first embodiment, the contact between the first mixture and the first extraction solvent is preferably carried out through distillation. The first embodiment is preferably a method in which a third mixture is obtained by mixing the first mixture of 1224yd and the above-described compound (X1) and the first extraction solvent, to make the first mixture and the first extraction solvent to be brought into contact with each other, and the third mixture is distilled, thereby manufacturing purified 1224yd not substantially containing the above-described compound (X1). The above-described third mixture may also contain, other than 1224yd, the compound (X1), and the first extraction solvent, other components such as 1-chloro-3,3,3-trifluoropropene (1233zd) and 1,1,1,2,3-pentafluoropropene (1225ye), but, a content of the other components is preferably set to 50 mol % or less of the entire third mixture.

When the third mixture is obtained by mixing the first mixture and the first extraction solvent, it is preferable to perform the mixing so that a molar ratio of the first extraction solvent with respect to 1224yd in the first mixture (referred to as "solvent ratio 1", hereinafter) becomes 0.4 to 200, from a viewpoint of efficiently separating 1224yd and the compound (X1). It is more preferable to perform the mixing so that the molar ratio becomes 1 to 100. From a viewpoint of obtaining purified 1224yd in the gas phase part, the relative volatility r1 in the solvent ratio in the above-described range is preferably larger than 1.15, and more preferably equal to or larger than 1.2. From a viewpoint of obtaining purified 1224yd in the liquid phase part, the relative volatility r1 in the solvent ratio in the above-described range is preferably smaller than 0.85, and more preferably equal to or smaller than 0.8. As a method of distilling the above-described third mixture, it is possible to use a method which has been conventionally well-known without particular limitation.

When the first embodiment includes the distillation process as described above, the distillation in the process corresponds to extractive distillation. In the present specification, "extractive distillation" is used from a perspective that it is used in the technical field of the present invention, particularly in a field of chemical engineering, and indicates one kind of distillation and separation methods used for separating an azeotropic composition, an azeotropic-like composition, liquid compositions which are difficult to be subjected to distillation and separation due to close boiling points, and so on. In the extractive distillation, an additional component is added to a composition made of a plurality of components to change a relative volatility of predetermined components, to thereby make it easy to perform distillation and separation. The additional component which is added to the composition made of the plurality of components described above is referred to as an extraction solvent. The extraction solvent indicates one which is in a liquid state at a room temperature and an atmospheric pressure, but, it may be one which exists in a liquid state under a reaction condition in a distillation column even if it is in a gaseous state at a room temperature and an atmospheric pressure.

The above-described first extraction solvent is preferably one capable of fulfilling a function as an extraction solvent in the extractive distillation.

Second Embodiment

A manufacturing method of purified 1224yd (Z) being a second embodiment of the present invention is a method in which a second mixture of 1224yd (Z) and a compound (X2) that forms an azeotropic composition or an azeotropic-like composition with 1224yd (Z) is brought into contact with a second extraction solvent to obtain purified 1224yd (Z) not substantially containing the above-described compound (X2).

The second extraction solvent is preferably one capable of making the relative volatility r2 greatly deviate from 1. When the relative volatility r2 greatly deviates from 1, the compound (X2) and 1224yd (Z) are easily separated, so that it is possible to efficiently manufacture purified 1224yd (Z).

In the second embodiment, a relative volatility between 1224yd (Z) and the compound (X2) in a state where the second extraction solvent is not added is set to a relative volatility r21, the above-described relative volatility when the second extraction solvent is added is set to a relative volatility r22, and the relative volatility r21 and the relative volatility r22 are compared.

When the relative volatility r22 is larger than the relative volatility r21, this means that an affinity of the compound (X2) with respect to the second extraction solvent is higher than an affinity of 1224yd (Z) with respect to the second extraction solvent. By using the second extraction solvent capable of making the relative volatility r22 to be larger than the relative volatility r21, it is easy to obtain purified 1224yd (Z) in a gas phase part by efficiently separating 1224yd (Z) and the compound (X2) from the second mixture.

When the relative volatility r22 is smaller than the relative volatility r21, this means that the affinity of the compound (X2) with respect to the second extraction solvent is lower than the affinity of 1224yd (Z) with respect to the second extraction solvent. By using the second extraction solvent capable of making the relative volatility r22 to be smaller than the relative volatility r21, it is easy to obtain purified 1224yd (Z) in a liquid phase part by efficiently separating 1224yd (Z) and the compound (X2) from the above-described second mixture.

From the above-described viewpoint, the second extraction solvent is preferably a solvent making the relative volatility r2 to be smaller than 0.85 or larger than 1.15, and it is more preferably a solvent making the relative volatility r2 to be equal to or smaller than 0.8 or equal to or larger than 1.20. When the relative volatility r2 is within the above-described range, it is easy to obtain purified 1224yd (Z) in the gas phase part or the liquid phase part.

The second extraction solvent may employ one similar to the first extraction solvent, and a preferable example thereof is also similar to that of the first extraction solvent.

In the second embodiment, the contact between the second mixture and the second extraction solvent is preferably carried out through distillation. The second embodiment is preferably a method in which a fourth mixture is obtained by mixing the second mixture of 1224yd (Z) and the above-described compound (X2) and the second extraction solvent, to make the second mixture and the second extraction solvent to be brought into contact with each other, and the fourth mixture is distilled, thereby obtaining purified 1224yd (Z) not substantially containing the above-described compound (X2). The above-described fourth mixture may also contain, other than 1224yd (Z), the compound (X2), and the second extraction solvent, other components such as 1-chloro-3,3,3-trifluoropropene (1233zd) and 1,1,1,2,3-pentafluoropropene (1225ye), but, a content of the other components is preferably set to 50 mol % or less of the entire fourth mixture.

When the fourth mixture is obtained by mixing the second mixture and the second extraction solvent, it is preferable to perform the mixing so that a molar ratio of the second extraction solvent with respect to 1224yd (Z) in the second mixture (referred to as "solvent ratio 2", hereinafter) becomes 0.4 to 200, from a viewpoint of efficiently separating 1224yd (Z) and the compound (X2). It is more preferable to perform the mixing so that the molar ratio becomes 1 to 100. From a viewpoint of obtaining purified 1224yd (Z) in the gas phase part, the relative volatility r2 is preferably larger than 1.15, and more preferably equal to or larger than 1.2. From a viewpoint of obtaining purified 1224yd (Z) in the liquid phase part, the relative volatility r2 is preferably smaller than 0.85, and more preferably equal to or smaller than 0.8.

As a method of distilling the above-described fourth mixture, it is possible to use a method which has been conventionally well-known without particular limitation. When the second embodiment includes the distillation process as described above, the distillation in the process corresponds to extractive distillation, similarly to the distillation in the process of distilling the above-described third mixture. The above-described second extraction solvent is preferably one capable of fulfilling a function as an extraction solvent in the extractive distillation, similarly to the above-described first extraction solvent.

Next, flows of substances in the embodiment of the present invention will be described by using a case, as an example, where the first extraction solvent having the affinity with respect to the compound (X1) and making the relative volatility r1 to be larger than 1.15 is used in the first embodiment using the extractive distillation.

A case where an extraction solvent having the affinity with respect to 1224yd and making the relative volatility r1 to be smaller than 0.85 is used, can be explained similarly except that the flow of 1224yd and the flow of the compound (X1) are only replaced. Further, the flows of the substances are similar also in a case of using a composition containing the first mixture and a compound other than the first mixture, in place of the first mixture. The flows of the substances are similar also in the second embodiment.

Each of the first mixture being the mixture of 1224yd and the compound (X1) and the first extraction solvent is supplied to an extractive distillation column which is operated through pressurization, for example. A timing at which the first extraction solvent is added does not matter in particular as long as the addition is performed before the extractive distillation. It is also possible that the third mixture obtained by adding the first extraction solvent to the first mixture is supplied to the extractive distillation column. However, from a viewpoint of efficiency of the distillation work, it is preferable that the third mixture is prepared in the extractive distillation column through a method such that the first extraction solvent is supplied to the extractive distillation column having the first mixture supplied thereto, and the distillation is performed simultaneously with the preparation.

A position at which the first extraction solvent is supplied in the extractive distillation column is preferably above a position at which the first mixture is supplied, and the first extraction solvent may be supplied to a position same as a position to provide a reflux. According to circumstances, the first extraction solvent may also be supplied to a stage same as that of the first mixture.

From a viewpoint of efficiently separating 1224yd and the compound (X1) through the extractive distillation, it is preferable to adjust a molar ratio of the first extraction solvent with respect to 1224yd in the first mixture so that the molar ratio falls within a range of the solvent ratio 1 described above. Note that since the solvent ratio 1 exerts influence on the degree of separation in the extractive distillation, it can be appropriately selected according to the chemical composition and the like of the first mixture to be subjected to the extractive distillation. Further, it is also possible to select the necessary number of stages of the extractive distillation column based on the solvent ratio 1.

When the boiling point of the first extraction solvent and the boiling point of 1224yd in the first mixture deviate sufficiently, and it is regarded that the component refluxed in the distillation column is only the 1224yd, the solvent ratio 1 can be regarded as a molar ratio of the first extraction solvent with respect to a reflux amount of the 1224yd.

The third mixture containing the first mixture and the first extraction solvent is subjected to the extractive distillation in the extractive distillation column. When the first mixture and the first extraction solvent are separately supplied into the distillation column, it is also possible that they are mixed in the distillation column to obtain the third mixture. For the extractive distillation, it is possible to use a generally used distillation apparatus, for example, a plate column, a packed column, or the like. Various conditions of the extractive distillation such as, for example, an operation temperature, an operation pressure, a reflux ratio, a total number of stages of the distillation column, a position of preparation stage, and a position of an extraction solvent supply stage, are not particularly limited, and can be appropriately selected for achieving the intended separation.

Besides, temperatures of a column top portion and a column bottom portion of the extractive distillation column are determined in accordance with the operation pressure and chemical compositions of a distillate and a bottom product. By taking temperatures of a condenser and a reheater provided in the column top portion and the column bottom portion into consideration, in order to economically perform the distillation operation, the temperature of the column top portion is preferably set to −60 to 100° C., and the temperature of the column bottom portion is preferably set to −30 to 250° C. The extractive distillation can be carried out through a batch mode, a continuous mode, or a semi-continuous mode, according to circumstances, in which the distillate and the bottom product are intermittently extracted or the preparation is intermittently performed. The first extraction solvent is required to be continuously supplied to the distillation apparatus.

By the extractive distillation, a distillate containing 1224yd as a main component can be obtained from the column top side of the extractive distillation column, and a bottom product containing the compound (X1) and the first extraction solvent can be obtained from the column bottom side of the extractive distillation column. In a manner as described above, it is possible to obtain purified 1224yd not substantially containing the compound (X1) as the distillate.

The bottom product obtained from the column bottom side of the extractive distillation column is preferably further distilled. The first extraction solvent and the compound (X1) contained in the bottom product have a large boiling point difference, so that they can be easily separated through a normal distillation operation. The first extraction solvent obtained in the distillation process can also be reused in the extractive distillation process.

EXAMPLES

Hereinafter, the present invention will be concretely described by using examples, but, the present invention is not limited to these examples.

(Measuring Method of Relative Volatility)

Hereinafter, an example of measuring a relative volatility (relative volatility r2) of each component contained in the 1224yd (Z) composition containing 1224yd (Z) and the compound (X2) will be described. As the 1224yd (Z) composition, a composition having a chemical composition represented in Table 1 (referred to as "composition A", hereinafter) was used. The above-described composition A contains 1224yd (Z) obtained when manufacturing 1224yd (Z) and the compounds (X2) as by-products. In the composition A, the relative volatility r2 between 1224yd (Z) and the compound (X2) was measured through the following method.

Specifically, in a cylinder of 100 mL whose inside was subjected to vacuum processing, 30 g of the composition A was prepared, and a temperature was raised to 40° C. by performing heating using an external heater. Subsequently, after a pressure became 0.14 MPaG (G indicates a gage pressure, hereinafter), retention was performed for one hour to stabilize the composition in the cylinder, and then samples were collected from a gas phase and a liquid phase. 1224yd (Z), and 1224yd (E), 226ca, 226cb, 1224zb, and 1224xe being the compounds (X2) in each of the samples in the gas phase and the liquid phase were respectively analyzed by gas chromatography (referred to as "GC", hereinafter), to thereby obtain chemical compositions of the respective components. As the GC, Agilent 7890 manufactured by Agilent Technologies was used. The same applies to the following examples and comparative examples. The obtained chemical composition was inserted into the aforementioned formula (2) to determine the relative volatility r2. Measured results are shown in Table 2.

Further, in a cylinder of 100 mL, 30 g of the composition A, and in addition to that, 30 g of methanol, acetone, hexane, ethanol, 1214ya, chloroform, or 225cb as a solvent were prepared, and in a manner similar to the above, the above-described relative volatility r2 was measured in a case where each of the solvents was added to the composition A. Note that the measurement of the relative volatility r2 described above when adding each of the solvents was performed by changing the conditions of the temperature and the pressure in the cylinder as shown in Table 2. The obtained values of the relative volatilities r2 are shown in Table 2.

TABLE 1

| Compound | mol % |
| --- | --- |
| 226ca | 2.978 |
| 226cb | 2.623 |
| 1224yd(Z) | 65.895 |
| 1224zb | 1.024 |
| 1224xe | 4.611 |
| 1224yd(E) | 21.917 |
| Others | 0.952 |
| Total | 100.000 |

TABLE 2

| | | Extraction solvent | | | | | | | | |
| --- | --- | --- | --- | --- | --- | --- | --- | --- | --- | --- |
| | | Not added | Methanol | | Acetone | | Hexane | | Ethanol | |
| Temperature | | 40° C. | 30° C. | 60° C. | 40° C. | 50° C. | 40° C. | 60° C. | 40° C. | 60° C. |
| Pressure [MPaG] | | 0.14 | 0.02 | 0.16 | 0.025 | 0.06 | 0.064 | 0.168 | 0.07 | 0.194 |
| Relative volatility r2 | 226ca | 1.020 | 1.282 | 1.274 | 1.282 | 1.289 | 0.961 | 0.953 | 1.137 | 1.170 |
| | 226cb | 1.058 | 1.297 | 1.294 | 1.313 | 1.374 | 0.758 | 0.734 | 1.028 | 1.072 |
| | 1224yd(Z) | 1.000 | 1.000 | 1.000 | 1.000 | 1.000 | 1.000 | 1.000 | 1.000 | 1.000 |

TABLE 2-continued

| | | | | | | | | | |
|---|---|---|---|---|---|---|---|---|---|
| 1224zb | 0.976 | 1.720 | 1.919 | 1.662 | 1.485 | 0.929 | 0.873 | 1.393 | 1.437 |
| 1224xe | 1.054 | 1.183 | 1.207 | 1.151 | 1.141 | 1.000 | 1.011 | 1.126 | 1.186 |
| 1224yd(E) | 1.070 | 1.197 | 1.216 | 1.083 | 1.087 | 1.029 | 1.054 | 1.189 | 1.248 |

| | | Extraction solvent | | | | | |
|---|---|---|---|---|---|---|---|
| | | 1214ya | | Chloroform | | 225cb | |
| Temperature | | 40° C. | 60° C. | 40° C. | 60° C. | 40° C. | 60° C. |
| Pressure [MPaG] | | 0.084 | 0.222 | 0.078 | 0.22 | 0.098 | 0.228 |
| Relative volatility r2 | 226ca | 1.034 | 1.060 | 0.900 | 1.001 | 1.020 | 1.144 |
| | 226cb | 0.864 | 0.809 | 1.075 | 1.117 | 1.051 | 1.140 |
| | 1224yd(Z) | 1.000 | 1.000 | 1.000 | 1.000 | 1.000 | 1.000 |
| | 1224zb | 0.892 | 0.891 | 0.856 | 0.922 | 1.039 | 1.041 |
| | 1224xe | 1.033 | 1.101 | 1.063 | 1.129 | 1.080 | 1.196 |
| | 1224yd(E) | 1.064 | 1.147 | 1.110 | 1.188 | 1.083 | 1.230 |

From Table 2, it is possible to understand the following. Each relative volatility r2 between 1224yd (Z) and 1224yd (E), 226ca, 226cb, 1224zb, or 1224xe in a state of adding no extraction solvent in the composition A can be 0.9 to 1.1 by adjusting the temperature or the pressure. Accordingly, 1224yd (E), 226ca, 226cb, 1224zb, and 1224xe correspond to the compounds (X2).

Each of the respective solvents of methanol, acetone, hexane, ethanol, 1214ya, chloroform, and 225cb is a solvent capable of making the relative volatility r2 between 1224yd (Z) and 1224yd (E), 226ca, 226cb, 1224zb, or 1224xe to be larger than 1.15 or smaller than 0.85, regarding at least one kind of 1224yd (E), 226ca, 226cb, 1224zb, and 1224xe.

Therefore, it is possible to consider that by using the solvent capable of making the relative volatility r2 to be larger than 1.15 among these solvents as the second extraction solvent, mixing the solvent with the second mixture of 1224yd (Z) and the compound (X2) to obtain the fourth mixture, and performing the extractive distillation on the fourth mixture, it is possible to obtain purified 1224yd (Z) in the gas phase part. Further, it is possible to consider that by using the solvent capable of making the relative volatility r2 to be smaller than 0.85 as the second extraction solvent, mixing the solvent with the second mixture of 1224yd (Z) and the compound (X2) to obtain the fourth mixture, and performing the extractive distillation on the fourth mixture, it is possible to obtain purified 1224yd (Z) in the liquid phase part.

The relative volatility r2 of a larger number of compounds (X2) becomes larger than 1.2 when methanol is used among the above-described solvents, so that in order to further obtain purified 1224yd (Z) in the gas phase part through the extractive distillation, it is preferable to use methanol as the second extraction solvent.

The value of the relative volatility r2 tends to deviate from 1 when the temperature is higher even when the same solvent is used, so that it can be considered that, in a predetermined temperature range, it is possible to easily separate 1224yd (Z) by performing the extractive distillation at a high temperature.

When the relative volatilities r2 were measured while changing the solvent ratios by using the composition A, and using methanol as the second extraction solvent, results as shown in Table 3 were obtained. Note that the solvent ratio is a molar ratio of methanol with respect to 1224yd (Z) in the composition A. The composition A is made of only 1224yd (Z) and the compound (X2), and corresponds to the second mixture. From Table 3, it can be understood that the relative volatility r2 regarding the compound (X2) becomes substantially 1.2 or more, and as the solvent ratio becomes higher, the relative volatility r2 between 1224yd (Z) and the compound (X2) is increased.

TABLE 3

| Extraction solvent | | Methanol | | | | |
|---|---|---|---|---|---|---|
| Pressure [MPaG] | | 0.2 | 0.2 | 0.2 | 0.2 | 0.2 |
| Solvent ratio 2 [mol/mol] (solvent/1224yd (Z) in second mixture) | | 15 (1/0.07) | 30 (1/0.03) | 60 (1/0.017) | 76 (1/0.013) | 3 (1/0.33) |
| Relative volatility r2 | 226ca | 1.256 | 1.242 | 1.226 | 1.355 | 1.226 |
| | 226cb | 1.537 | 1.667 | 2.031 | 1.827 | 1.405 |
| | 1224yd(Z) | 1.000 | 1.000 | 1.000 | 1.000 | 1.000 |
| | 1224zb | 1.941 | 2.016 | 2.121 | 2.285 | 1.216 |
| | 1224xe | 1.223 | 1.263 | 1.290 | 1.312 | 1.197 |
| | 1224yd(E) | 1.204 | 1.226 | 1.250 | 1.269 | 1.216 |

Example 1

From a 40th stage counted from a column top portion of an extractive distillation column with 65 stages, a composition having a chemical composition represented in Table 4 (referred to as "composition B", hereinafter) was continuously supplied, and from a 10th stage counted from the top, methanol being the extraction solvent was continuously supplied. The composition B is made of only 1224yd (Z) and the compound (X2), and corresponds to the second mixture. A pressure in the extractive distillation column was set to 0.1 to 0.15 MPaG, a column top temperature was set to 35 to 45° C., and the extractive distillation was continuously performed at a reflux ratio (reflux amount/distillate amount) of 20. Next, a distillate was extracted from the column top side of the extractive distillation column, and a bottom product was extracted from the column bottom side of the extractive distillation column.

A molar ratio of the extraction solvent with respect to the reflux amount was 2.87. In this distillation, it is possible to consider that the reflux amount is an amount of 1224yd (Z) in the second mixture having a boiling point lower than that of the extraction solvent, liquefied by being cooled in the top portion of the distillation column. Therefore, the molar ratio of the extraction solvent with respect to the reflux amount can be set to the solvent ratio 2 (a molar ratio of the extraction solvent with respect to 1224yd (Z) in the second mixture). A molar ratio between a supply amount of the extraction solvent continuously supplied from a stage in the middle of the extractive distillation column and a supply amount of the second mixture was 92.8.

TABLE 4

| Compound | mol % |
|---|---|
| 1224yd(Z) | 66.2617 |
| 1224yd(E) | 22.8129 |
| 226ca | 2.4763 |
| 226cb | 2.6988 |
| 1224xe | 4.7791 |
| 1224zb | 0.6074 |
| Others | 0.3638 |
| Total | 100.0000 |

Next, the bottom product obtained from the column bottom side of the extractive distillation column was supplied to a solvent recovery column to be distilled, and the extraction solvent was separated to be recovered. Chemical compositions of the bottom product after the extraction solvent was separated therefrom as above and the distillate extracted from the column top side of the extractive distillation column described above were respectively analyzed by using the GC. Analysis results are shown in Table 5.

Examples 2 to 6

The extractive distillation was continuously performed similarly to the example 1 except that it was performed under conditions represented in Table 5 while supplying the composition B and methanol to an extractive distillation column with 65 stages, setting a column top temperature to 35 to 45° C., and setting a pressure to 0.1 to 0.15 MPaG. Subsequently, chemical compositions of a distillate extracted from the column top side and a bottom product extracted from the column bottom side and then the extraction solvent was separated therefrom were analyzed by using the GC similarly to the example 1. Analysis results are shown in Table 5.

Comparative Example

The composition B was supplied to an extractive distillation column with 100 stages, a column top temperature was set to 35 to 45° C., a pressure was set to 0.1 to 0.15 MPaG, and the distillation was continuously performed at a reflux ratio of 50. Subsequently, a distillate was extracted from the column top side, and a bottom product was extracted from the column bottom side.

Next, chemical compositions of the distillate and the bottom product extracted from the extractive distillation column were analyzed by using the GC similarly to the example 1. Analysis results are shown in Table 5.

TABLE 5

|  | Example 1 | Example 2 | Example 3 | Example 4 |
|---|---|---|---|---|
| Reflux ratio | 20 | 10 | 35 | 50 |
| Solvent ratio 2 (ratio of extraction solvent with respect to reflux amount) [mol/mol] | 2.87 | 1.73 | 1.72 | 1.72 |
| Supply amount (extraction solvent/second mixture) [mol/mol] | 92.8 | 92.8 | 92.8 | 92.8 |

| Chemical composition (mol %) | Distillate | Bottom product | Distillate | Bottom product | Distillate | Bottom product | Distillate | Bottom product |
|---|---|---|---|---|---|---|---|---|
| 1224yd(Z) | 99.456 | 19.256 | 97.243 | 30.384 | 99.568 | 18.926 | 99.573 | 19.565 |
| 1224yd(E) | 0.000 | 52.109 | 2.123 | 46.037 | 0.000 | 51.866 | 0.000 | 53.077 |
| 226ca | 0.000 | 6.886 | 0.000 | 5.251 | 0.000 | 6.025 | 0.000 | 6.757 |
| 226cb | 0.000 | 7.255 | 0.000 | 5.458 | 0.000 | 7.002 | 0.000 | 7.108 |
| 1224xe | 0.000 | 12.358 | 0.000 | 9.923 | 0.000 | 10.553 | 0.000 | 11.357 |
| 1224zb | 0.000 | 1.021 | 0.000 | 1.391 | 0.000 | 1.111 | 0.000 | 1.021 |
| Others | 0.544 | 1.115 | 0.634 | 1.557 | 0.432 | 4.517 | 0.427 | 1.115 |
| Total | 100.000 | 100.000 | 100.000 | 100.000 | 100.000 | 100.000 | 100.000 | 100.000 |

|  | Example 5 | Example 6 | Comparative example |
|---|---|---|---|
| Reflux ratio | 50 | 10 | 50 |
| Solvent ratio 2 (ratio of extraction solvent with respect to reflux amount) [mol/mol] | 0.77 | 19.14 | — |
| Supply amount (extraction solvent/second mixture) [mol/mol] | 36.8 | 183.8 | — |

TABLE 5-continued

| Chemical composition (mol %) | Distillate | Bottom product | Distillate | Bottom product | Distillate | Bottom product |
|---|---|---|---|---|---|---|
| 1224yd(Z) | 99.553 | 19.323 | 99.156 | 16.357 | 94.913 | 22.207 |
| 1224yd(E) | 0.000 | 52.156 | 0.000 | 58.598 | 0.536 | 54.090 |
| 226ca | 0.000 | 6.735 | 0.000 | 6.343 | 1.023 | 5.385 |
| 226cb | 0.000 | 6.894 | 0.000 | 6.722 | 1.053 | 5.256 |
| 1224xe | 0.000 | 11.675 | 0.000 | 10.211 | 0.288 | 11.097 |
| 1224zb | 0.000 | 1.331 | 0.000 | 1.435 | 1.577 | 0.194 |
| Others | 0.447 | 1.886 | 0.844 | 0.334 | 0.611 | 1.771 |
| Total | 100.000 | 100.000 | 100.000 | 100.000 | 100.000 | 100.000 |

From Table 5, it can be understood that in each of the examples 1 to 6 in which the extractive distillation was performed by adding methanol to the composition B, it is possible to obtain, from the column top side of the extractive distillation column, purified 1224yd (Z) that contains 1224yd (Z) at a quite high concentration, and that does not substantially contain the compound (X2) that forms the azeotropic-like composition with 1224yd (Z).

According to the present invention, it is possible to efficiently obtain, from a mixture containing 1224yd and a compound forming an azeotropic-like composition with the 1224yd, purified 1224yd not substantially containing the above-described compound, which provides high industrial availability. Further, it is possible to efficiently obtain purified 1224yd (Z) from a mixture containing 1224yd (Z) and a compound forming an azeotropic composition or an azeotropic-like composition with 1224yd (Z), which provides high industrial availability.

What is claimed is:

1. A method of manufacturing purified 1-chloro-2,3,3,3-tetrafluoropropene, the method comprising:
   making a first mixture of 1-chloro-2,3,3,3-tetrafluoropropene and a compound (X1) that forms an azeotropic composition or an azeotropic-like composition with 1-chloro-2,3,3,3-tetrafluoropropene, and
   contacting the first mixture with a first extraction solvent to obtain purified 1-chloro-2,3,3,3-tetrafluoropropene not substantially comprising the compound (X1).

2. A method of manufacturing purified 1-chloro-2,3,3,3-tetrafluoropropene (Z), the method comprising:
   making a second mixture of 1-chloro-2,3,3,3-tetrafluoropropene (Z) and a compound (X2) that forms an azeotropic composition or an azeotropic-like composition with 1-chloro-2,3,3,3-tetrafluoropropene (Z), and
   contacting the second mixture with a second extraction solvent to obtain purified 1-chloro-2,3,3,3-tetrafluoropropene (Z) not substantially comprising the compound (X2).

3. The method of claim 1, wherein the compound (X1) is a compound which exhibits a relative volatility between 1-chloro-2,3,3,3-tetrafluoropropene and the compound (X1) in the first mixture of 0.9 to 1.1.

4. The method of claim 2, wherein the compound (X2) is a compound which exhibits a relative volatility between 1-chloro-2,3,3,3-tetrafluoropropene (Z) and the compound (X2) in the second mixture of 0.9 to 1.1.

5. The method of claim 1, wherein the first extraction solvent is a solvent capable of making the relative volatility between 1-chloro-2,3,3,3-tetrafluoropropene and the compound (X1) smaller than 0.85 or larger than 1.15.

6. The method of claim 2, wherein the second extraction solvent is a solvent capable of making the relative volatility between 1-chloro-2,3,3,3-tetrafluoropropene (Z) and the compound (X2) smaller than 0.85 or larger than 1.15.

7. The method of claim 1, wherein the first extraction solvent is one selected from the group consisting of an alcohol having 1 to 3 carbon atoms and a carbonyl compound having 2 to 4 carbon atoms other than the carbon atom of a carbonyl group.

8. The method of claim 2, wherein the second extraction solvent is one selected from the group consisting of an alcohol having 1 to 3 carbon atoms and a carbonyl compound having 2 to 4 carbon atoms other than the carbon atom of a carbonyl group.

9. The method of claim 1, further comprising:
   obtaining a third mixture by mixing the first mixture and the first extraction solvent, and
   distilling the third mixture.

10. The method of claim 9, wherein the mixing is performed at a molar ratio of the first extraction solvent with respect to 1-chloro-2,3,3,3-tetrafluoropropene of 0.4 to 200.

11. The method of claim 2, further comprising:
   obtaining a fourth mixture by mixing the second mixture and the second extraction solvent, and
   distilling the fourth mixture.

12. The method of claim 11, wherein the mixing is performed at a molar ratio of the second extraction solvent with respect to 1-chloro-2,3,3,3-tetrafluoropropene (Z) of 0.4 to 200.

13. The method of claim 1, wherein the first mixture is an azeotropic composition or an azeotropic-like composition.

14. The method of claim 2, wherein the second mixture is an azeotropic composition or an azeotropic-like composition.

15. The method of claim 1, wherein the compound (X1) is 1-chloro-1,2,2,3,3,3-hexafluoropropane, 1-chloro-1,1,2,2,3,3-hexafluoropropane, 1-chloro-1,3,3,3-tetrafluoropropene, or 2-chloro-1,3,3,3-tetrafluoropropene.

16. The method of claim 2, wherein the compound (X2) is 1-chloro-1,2,2,3,3,3-hexafluoropropane, 1-chloro-1,1,2,2,3,3-hexafluoropropane, 1-chloro-1,3,3,3-tetrafluoropropene, 2-chloro-1,3,3,3-tetrafluoropropene, or 1-chloro-2,3,3,3-tetrafluoropropene (E).

17. The method of claim 1, wherein the first extraction solvent is a saturated hydrocarbon having 5 to 12 carbon atoms, a halogenated hydrocarbon having 1 to 10 carbon atoms which does not have an ether bond, an alcohol having 1 to 3 carbon atoms, or a carbonyl compound.

18. The method of claim 1, wherein the first extraction solvent is methanol, ethanol, or acetone.

19. The method of claim 2, wherein the second extraction solvent is a saturated hydrocarbon having 5 to 12 carbon atoms, a halogenated hydrocarbon having 1 to 10 carbon atoms which does not have an ether bond, an alcohol having 1 to 3 carbon atoms, or a carbonyl compound.

20. The method of claim 2, wherein the first extraction solvent is methanol, ethanol, or acetone.

* * * * *